United States Patent
Gilbert

(10) Patent No.: US 7,155,990 B2
(45) Date of Patent: Jan. 2, 2007

(54) METHOD AND APPARATUS FOR DETERMINING A DOWNHOLE FLUID SAMPLE VOLUME

(75) Inventor: Gregory N. Gilbert, Sugar Land, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 11/023,335

(22) Filed: Dec. 27, 2004

(65) Prior Publication Data

US 2006/0137479 A1 Jun. 29, 2006

(51) Int. Cl.
*G01N 1/00* (2006.01)

(52) U.S. Cl. .................. 73/864.62; 73/152.26

(58) Field of Classification Search ............. 73/864.34, 73/864.51, 864.61, 864.62, 864.63, 864.73, 73/864.91, 152.23, 152.24, 152.25, 152.26; 166/264
See application file for complete search history.

(56) References Cited

U.S. PATENT DOCUMENTS

| | | | |
|---|---|---|---|
| 3,530,933 A | 9/1970 | Whitten | |
| 3,577,783 A | 5/1971 | Whitten | |
| 3,611,799 A * | 10/1971 | Davis | 73/152.24 |
| 3,667,080 A | 6/1972 | Persson | |
| 3,793,888 A * | 2/1974 | Rosenwald | 73/864.62 |
| 3,952,588 A | 4/1976 | Whitten | |
| 4,308,144 A * | 12/1981 | Saito | 210/620 |
| 4,339,948 A | 7/1982 | Hallmark | |
| 4,583,589 A * | 4/1986 | Kasevich | 166/60 |
| 4,879,900 A | 11/1989 | Gilbert | |
| 4,922,764 A * | 5/1990 | Welker | 73/864.62 |
| 4,930,361 A * | 6/1990 | Nimberger | 73/864.62 |
| 4,936,139 A | 6/1990 | Zimmerman et al. | |
| 5,620,052 A * | 4/1997 | Turner | 166/348 |

* cited by examiner

*Primary Examiner*—Robert Raevis
(74) *Attorney, Agent, or Firm*—Browning Bushman P.C.

(57) ABSTRACT

A formation test tool 10 for obtaining a downhole fluid sample from a formation of interest 30 and returning the sample to the surface of a well includes a cylinder 12 forming a fluid sample chamber therein, and a piston 20 sealingly movable within the cylinder and separating the fluid sample from a cushioning fluid. A fluid line 24 connects the formation of interest to the fluid sample chamber, and a valve 26 controls fluid flow along the fluid line. In one embodiment, a magnet 76 supported on the piston outputs signals indicative of the position of the piston and thus the volume of the fluid sample within the cylinder. A meter 74 is movable along the exterior of the cylinder 12 for determining the position of the magnet within the cylinder, such that the volume of sampled fluid in the cylinder can be determined at the surface.

12 Claims, 3 Drawing Sheets

METHOD AND APPARATUS FOR DETERMINING A DOWNHOLE FLUID SAMPLE VOLUME

FIELD OF THE INVENTION

The invention relates to downhole formation test tools used to obtain one or more fluid samples from one or more formations of interest. More particularly, the invention relates to a technique for determining the volume of the one or more retrieved fluid samples at the surface.

BACKGROUND OF THE INVENTION

Formation test tools conventionally collect fluid samples in a sample chamber which has a known volumetric capacity, although the volume of the actual fluid sample taken downhole may not be known. A sample tool typically includes a cylinder fitted with an end cap and a separator piston for sealing engagement with the inside diameter of the cylinder. The volume within the cylinder between the end cap and the separator piston determines the volume occupied by the fluid sample. Due to various types of buffering systems used in formation test tools and the cooling effects on the fluid sample as it is retrieved to the surface, the volume of the collected sample at surface temperature and pressure is unknown.

One type of sample chamber arrangement utilizes an air cushion to buffer the formation fluid flowing into the chamber. A flow line conventionally connects a packer associated with the formation test tool to the inlet of the air cushioned sample chamber. Prior to sampling, the separator piston is in an uppermost position adjacent the end cap, and the volume below the separator piston is filled with air, usually at atmospheric pressure. When a sample formation fluid is to be collected, a flow line control valve is opened to fluidly connect the flow line to the inlet of the sample chamber. Formation pressure is substantially higher than air pressure below the separator piston, such that the formation fluid pushes the separator piston downward, thereby filling the chamber with formation fluid. The separator piston will continue to move downward until pressure across the separator piston is substantially equalized. The flow line control valve may then be closed, trapping the collected sample within the sample chamber.

Another formation test tool utilizes a liquid cushion as a buffer to control the rate at which formation fluid would fill the chamber. The buffer fluid below the separator piston is a relatively incompressible fluid, such as water or ethylene glycol. When the control valve is open, pressurized formation fluid acts on the separator piston forcing the buffer liquid through a restriction or choke. The region below the choke is initially filled with air at atmospheric pressure. Collected fluid pressure thus forces the buffer liquid through the choke and into the air filled choke chamber, thereby compressing the air. The separator piston will continue to move down until the pressure of the compressed air is approximately equal to the formation pressure, at which time the control valve may be closed to trap the collected sample within the cylinder.

Yet another technique for collecting downhole fluid samples utilizes a downhole pump as part of the formation test tool. The pump is connected to the flow line of the tool which is in fluid communication with the downhole formation of interest. The outlet of the pump is directed to the inlet of the sample chamber. The lower side of a separator piston is exposed to wellbore fluid at hydrostatic pressure. As the chamber is filled, the pressure of the fluid sample is increased by the pump from approximately formation pressure to a value equal to or higher than hydrostatic pressure. As formation fluid is pumped into the chamber, the separator piston moves downward, displacing the well fluid below the piston. Downward motion of the piston continues until the piston reaches its full extent of travel. The possibility of a flow line plugging during the sample filling procedure reduces the probability of a desired volumetric sample in the chamber.

Yet another formation test tool utilizes nitrogen or another compressible gas pressurized to downhole conditions to compensate for sample contraction upon cooling when the sample is retrieved to the surface. A nitrogen compensated sample chamber is separated by a piston adjacent the upper end cap when formation fluid is initially input to the cylinder. Nitrogen gas is contained between the separator piston and a lower charging piston. Wellbore fluid at hydrostatic pressure is exposed to the lower side of the charging piston. The outlet of the downhole pump is directed to the inlet of the sample chamber. As the chamber is filled, the separator piston, the nitrogen gas and the charging piston are pushed downward until the charging piston reaches its full extent of travel. Additional pumping displaces the separator piston, compressing the nitrogen charge. Once over pressurized to a desired value, the flow line control valve is closed to trap the collected sample.

U.S. Pat. No. 3,530,933 discloses a formation sampling tool for sampling downhole fluids. The tool includes an annular sealing pad for engagement with the wellbore surface. The flow of the fluid sample may be regulated for limiting the entrance of mudcake and formation materials that may plug the sampling system.

U.S. Pat. No. 3,577,783 discloses a downhole sampling tool with two pistons of a differential diameter within a cylinder. A delay is provided by a choke in a branch conduit or by a check valve and piston cylinder assembly in the branch conduit.

U.S. Pat. No. 3,677,080 discloses a formation sampling tool run on a logging cable. Pressure balancing pistons prevent hydrostatic pressures from interfering with tool mechanical functions.

U.S. Pat. No. 3,952,588 discloses a tool with a movable chamber expanded to draw mudcake and plugging materials into a receiving chamber. The chamber is shifted to thereafter communicate a screened entry port with the isolated formation.

U.S. Pat. No. 4,339,948 discloses a well formation test apparatus with a sealing pad arrangement to seal the test region and permit the flow of formation fluid from the region. A pressure detector senses and indicates a buildup of pressure from the fluid sample.

U.S. Pat. No. 4,879,900 discloses a formation tester with multiple sample storage containers and an equalizing valve to selectively isolate a snorkel from the fluid and pressures in the well. A control valve system operates backup shoes and a snorkel seal until testing is complete.

U.S. Pat. No. 4,936,139 discloses a formation test tool which utilizes a straddle packer to allow formation specimens to be taken at large flow rates.

A significant disadvantage of prior art formation test tools is that the operator at the surface cannot reliably verify the volume of fluid within the test tool. When the sample chamber is retrieved to the surface, the sample fluid cools and shrinks to reduce the sample pressure. This reduction in pressure will reposition the separator piston until a piston equilibrium pressure is established on both sides of the piston. Not being able to determine the volume of the downhole collected sample has significant drawbacks, since the sample cylinder may be shipped at considered expense to a laboratory for analysis only to determine that fluid has not been properly collected due to a leak in the system or due to a malfunction of the equipment. The operator at the surface may use a pressure gauge to determine the pressure of the sample fluid at the surface, but the inability to determine the volume of the sample fluid does not allow a meaningful correlation between known or presumed downhole temperature and pressure conditions, and the affect of the cooler surface temperature and lower pressure conditions on the sampled fluid.

The disadvantages of prior art are overcome by the present invention. Improved equipment and techniques for determining the volume at the surface of a transportable sample cylinder which houses downhole fluids may be made before shipment to a laboratory for sample analysis.

SUMMARY OF THE INVENTION

In one embodiment, a formation test tool is utilized for obtaining a downhole fluid sample from one or more formations of interest and returning the sample to the surface of the well. The test tool comprises a non-ferrous cylinder forming a fluid sample chamber therein, and a non-ferrous piston sealingly movable within the cylinder and separating the fluid sample from a cushioning fluid. A fluid line interconnects the formation of interest to the fluid sample chamber, and a valve controls fluid flow along the fluid line. A magnet supported on the piston outputs signals indicative of the volume of a fluid sample within the cylinder by providing an indication of the piston position within the cylinder. When the test tool is at the surface, a sensor may be moved axially along the exterior of the cylinder and readings from the sensor used to determine the position of the magnet and thus the volume of collected fluid.

In an alternate embodiment, a non-ferrous material cylinder may be used with a ferrous material piston, such that a transformer coil or other magnetic test tool external of the cylinder may be used at the surface for determining the piston position within the cylinder. In another embodiment, a sensor external of the cylinder may sense the position of a radioactive pellet on the piston to determine the piston position. In yet another embodiment, an acoustic sensor external of the cylinder may be responsive to the difference between fluid within the cylinder and the solid material of the piston, and thereby detect the fluid/piston interface and thus determine the position of the piston within the cylinder.

The formation test tool of the present invention is thus able to reliably determine the volume of the fluid within the transportable sample cylinder at the surface. This determination ensures that the cylinder contains the proper fluid sample before it is shipped to a laboratory for sample analysis, and also allowing the operator to correlate between known or presumed downhole temperature and pressure conditions and the cooler surface temperature and lower pressure conditions of the sample fluid at the surface.

These and further features and advantages of the present invention will become apparent from the following detailed description, wherein reference is made to the figures in the accompanying drawings.

DESCRIPTION OF THE ILLUSTRATED EMBODIMENTS

Various designs of formation sampling systems may benefit from the improvements provided by the present invention. Simplified sampling systems accordingly are illustrated in FIGS. 1–4, and improvements to the sampling system are shown in greater detail in FIGS. 5–9. Those skilled in the art of sampling systems will recognize that the various techniques as disclosed herein for determining the volume of the sampled fluid within the sampling system cylinder while at the surface may be applied to the different embodiments shown in FIGS. 1–4, or to variations of sampling systems which are modifications to these embodiments.

Figures 1, 2:
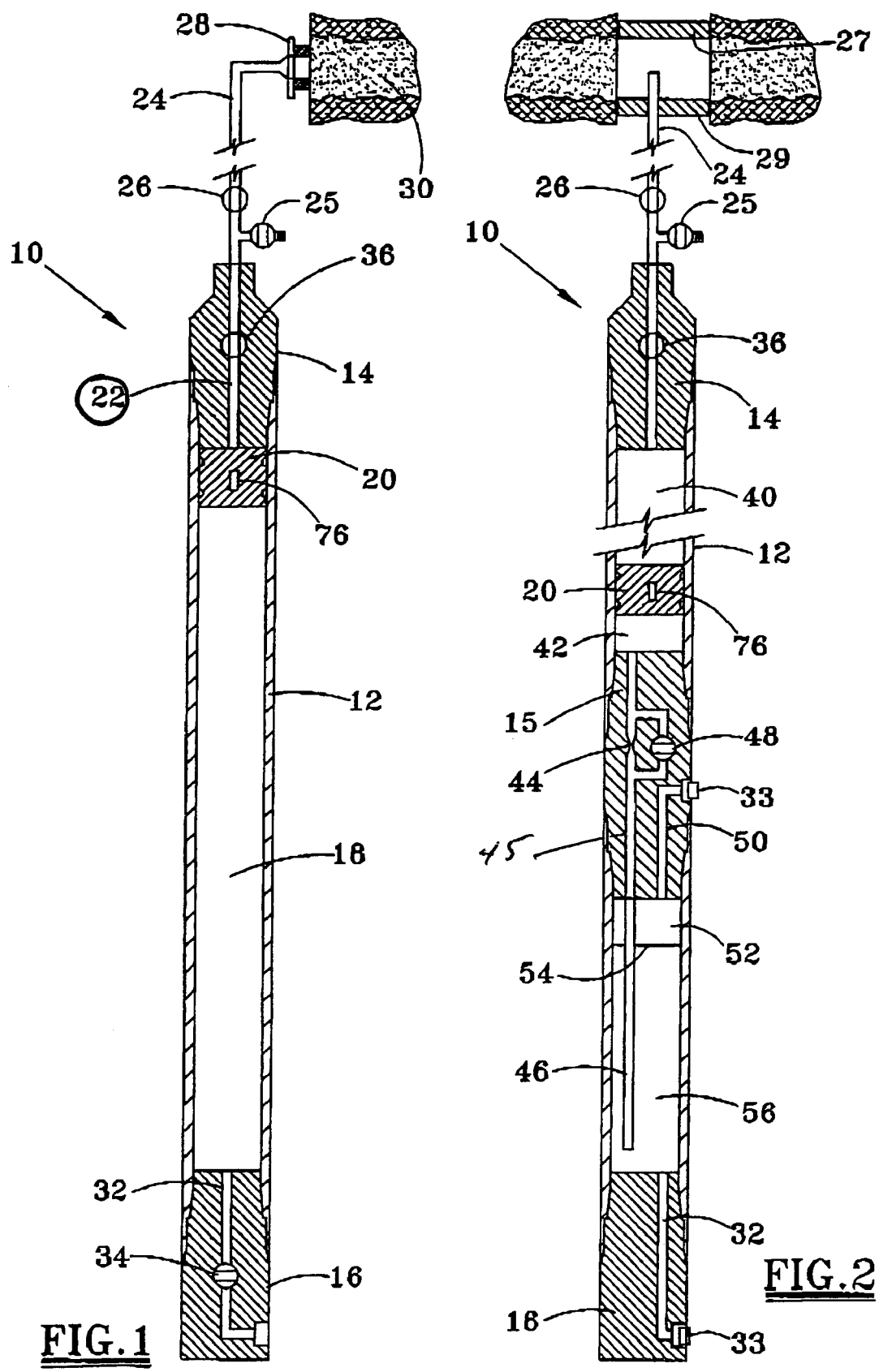
FIG. 1 illustrates a simplified version of an air cushioning sample test tool with a packer element sealed with a formation of interest.
FIG. 2 illustrates a water cushioned sample chamber tool with straddle packers sealing the formation of interest.

FIG. 1 illustrates a downhole fluid sampling system or test tool 10 including a sleeve-shaped cylinder 12 which forms a fluid sample chamber 18 therein. Cylinder 12 is substantially closed by an upper end cap 14 and lower end cap 16, with chamber 18 between the end caps initially containing low pressure air. A separator piston 20 movably sealed to the cylinder 12 initially is positioned in the upper end of the cylinder adjacent the end cap 14 when the sampling system is run in the well, and in response to the fluid sample pressure which is greater than the air pressure, the separator piston 20 moves downward, thereby compressing the air until the air pressure on the lower side of the piston is substantially equal to the fluid sample pressure on the upper side of the piston. At this time, the piston 20 may thus move downward from a position adjacent the upper end cap 14 to a location spaced slightly above the lower end cap 16.

The upper end cap 14 includes a fluid passageway 22 therein for transmitting formation fluid into the cylinder and to the top side of the separator piston 20, with an isolation valve 36 located along the flow path 22 in the upper end cap 14. A fluid line 24 extends from the upper end cap 14 to the formation of interest 30, and a flow line control valve 26 is positioned along the flow line 24 for controlling the fluid flow from the formation to the sampling cylinder. FIG. 1 further illustrates an annular packer element 28 for sealing engagement with the face of formation 30, so that formation fluid passes through the center of packer element 28 and to the flow line 24, and then to the sample cylinder 12. A lower end cap 16 also has a flow line 32 therein which communicates between the chamber 18 and exterior of the sleeve 12, with a normally closed valve 34 controlling the release of fluid along the flow line 32. A short T-line off line 24 includes a valve 25 for selectively receiving a pressure gauge when the sampling system is at the surface. Those skilled in the art will appreciate that the valve 25 remains closed when the tool is downhole, and that a pressure gauge (not shown) may be fluidly connected to the outlet of the valve 25 at the surface, and the valve 25 briefly opened to determine the pressure of the test fluid in the cylinder 12.

The fluid chamber 18 within the cylinder 12 thus initially serves as an air chamber for atmospheric air. The flow line control valve 26 is open to introduce formation fluid into the interior of the sleeve 12, thereby forcing the piston 20 downward. As the piston 20 moves downward toward the end cap 16, most of this chamber becomes a fluid sample chamber, with the air compressed by movement of the separator piston 20 such that compressed air exists between the piston 20 and the lower end cap 16. Once the pressure of the compressed air below the piston 20 and the fluid sample above the piston 20 are at substantially the same pressure, the flow line control valve 26 may be closed, thereby trapping the collected sample within the cylinder 12. When the cylinder 12 is retrieved to the surface, the contained formation sample cools and thus shrinks, thereby reducing the sample pressure. Reduction of sample pressure repositions the piston 20 until equilibrium is again established between the compressed air side and the sample side of the piston 20.

FIG. 2 illustrates an alternate arrangement wherein water, ethylene glycol, oil, or another selected incompressible fluid may be used as the buffer fluid. The flow line 24 may be as discussed above in FIG. 1 to provide fluid communication with the interior of the cylinder 12. In the FIG. 2 embodiment, an upper and lower packer 27, 29 are used to isolate fluid within formation 30 from the remainder of the wellbore. Any of the embodiments shown in FIGS. 1–4 may be used with the packer element 28 as shown in FIG. 1 or the straddle packers 27 and 29 shown in FIG. 2. Central member or choke sub 15 is fixed within the cylinder 12. The separator piston 20 initially may be positioned substantially adjacent the upper end cap 14, with the space between the piston and the central member 15 being filled with water. The space below the member 15 and the lower end cap 16 may initially be filled with air at atmospheric pressure. A vent tube 46 may pass water from above the central member 15 to below the central member 15 and through a choke 44 positioned along the flow path 45 within the member 15. A bypass valve 48 may be used at the surface to recycle chamber/piston management. Flow line 50 fluidly connects the chamber below the central member 15 to the exterior of cylinder 12. Both the flow line 32 in lower end cap 16 and the outlet from flow line 50 in the central member 15 may each be closed by plug 33.

When the flow line control valve 26 is open, formation pressure acts on the separator piston 20 and forces the buffer fluid, which may be water, ethylene glycol, oil or another selected incompressible liquid, through the restriction or choke 44, thereby establishing a threshold flowing pressure at which the formation fluid enters the chamber. The chamber 56 below the central member 15 and above the lower end cap 16 may be referred to as a choke chamber. Formation fluid forces the water through the choke and into the air filled (or gas filled) choke chamber 56, thereby compressing the air. Space 52 below central member 15 may thus be compressed air, with the interface 54 shown between the compressed air and the liquid. The separator piston 20 continues to move downward until the pressure of the compressed air is approximately equal to the formation pressure. The flow line control valve 26 may then be closed to trap the collected sample within the cylinder.

Figure 3:
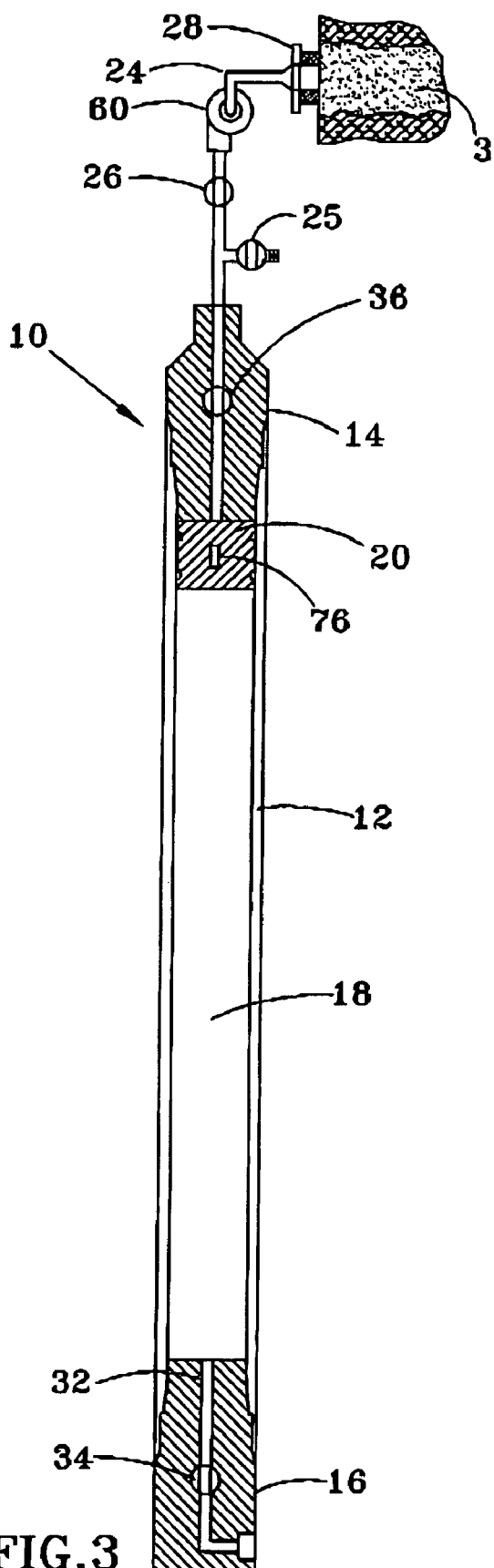
FIG. 3 illustrates a sampling tool with a hydrostatic balanced sample chamber and a pump along the flow line.

Referring now to FIG. 3, the downhole pump 60 is included within the sampling system or test tool 10, with the inlet of the pump connected with the downhole formation of interest 30 and the outlet of the pump being passed to the cylinder 12. Initially, the piston 20 again may be provided in the upper portion of the chamber 18 adjacent the upper end cap 14. The lower side of the piston 20 is thus exposed to wellbore fluid at hydrostatic pressure, since valve 34 is open to provide fluid communication along flow path 32 from the interior of the cylinder 12 to the exterior of the cylinder 12. Downward motion of the piston 20 continues until piston 20 reaches its full extent of travel and rests against the upper surface of the lower end cap 16.

Figure 4:
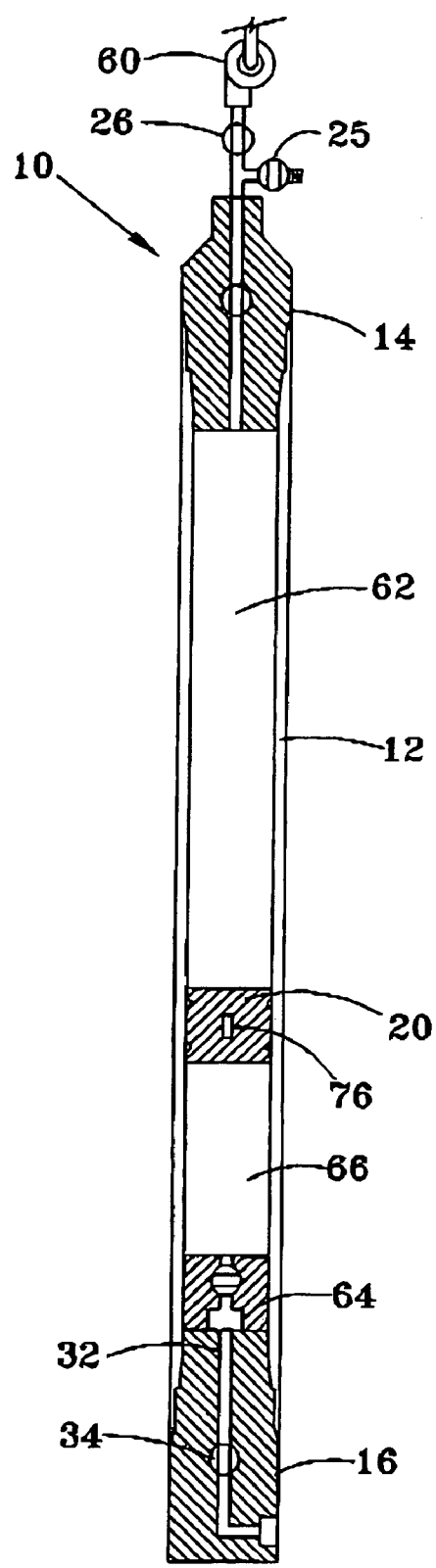
FIG. 4 illustrates a nitrogen compensated sample chamber tool.

FIG. 4 illustrates yet another configuration for a sampling system which utilizes an compressible gas, typically nitrogen, pressurized to downhole conditions to compensate for sample contraction upon cooling. A pump 60 and valves 26 and 25 are provided, as with the prior embodiment. The separator piston 20 is thus initially positioned adjacent the upper end cap 14, and nitrogen gas is contained in the space 66 between the separator piston 20 and the charging piston 64, which is sealed to cylinder 12 and does not pass fluid through piston 64. Wellbore fluid at hydrostatic pressure is exposed to the lower side of the charging piston 64, since valve 34 is open to provide fluid flow along the flow line 32 in the lower end cap 16. The outlet from the downhole pump is directed to the cylinder 12, and as a sample chamber is filled, the separator piston, the nitrogen gas and the charging piston are pushed downward until the charging piston reaches its full extent of travel, as shown in FIG. 4. Additional pumping moves the separator piston 20 further downward, compressing the nitrogen charge. Once overpressurized to the desired level, the flow line control valve 26 may be closed and with the collected sample trapped within the cylinder.

Figure 5:
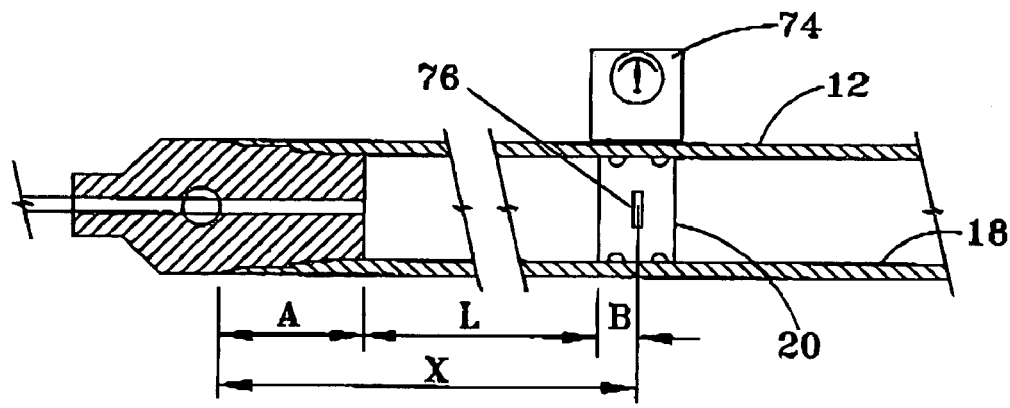
FIG. 5 illustrates a portion of the sample cylinder shown in FIG. 1 and a sensor for determining the position of the magnet within the sample chamber.

FIG. 5 illustrates a separator piston 20 within a portion of the sleeve 12, with a magnet 76 supported on the separator piston, and preferably positioned within the separator piston. Due in part to the corrosive nature of the fluids contained within the cylinder 12, the cylinder 12 and the piston 20 preferably may be fabricated from a high nickel alloy, such as inconel 718 or a titanium alloy. Besides being corrosion resistant, these materials are relatively non-magnetic.

The magnet 76 within the piston 20 may be disk shaped, and typically may be an Al—Ni—Co or Sm—Co material. The magnet 76 is fixed coaxially within the separator piston 20 and is magnetized along its axis, which is substantially coaxial with the axis of the cylinder 12. Once the collected sample is brought to the surface, a gauss meter 74 may be used to positively locate the magnet position and therefore the position of the piston, which thereby determines the size of the sample chamber containing the formation fluids. The gauss meter may be slid along the exterior of the sleeve 12 until the precise position of the magnet is located, which for the depicted embodiment corresponds to the middle of the magnetic field. Knowing the precise location of the separator piston within the sample chamber, an external measurement may be taken and used to calculate the contained sample volume. The length X between the end of the sleeve threads and the magnet position may thus be measured, with measurements A and B known, thereby allowing for the determination of measurement L. The volume of sampled fluid may thus be a function of the cross-sectional area of the chamber 18 and the length of measurement L.

The technique as disclosed herein allows for the determination of the precise volume of collected sample prior to shipment of the cylinder to a laboratory. A typical sample chamber may have a length of approximately 1 to 2 meters, and a volume of from 500 cc to a 1000 cc. The technique of this invention may be capable of determining the volume of the sample fluid to less than about 5 cc.

For each of the embodiments discussed above as well as the embodiments discussed below, the flow line 24 is shown positioned above the test tool and the separator piston 20 initially is in engagement or substantially in engagement with the upper end cap 14, so that the piston 20 moves downward as a sample is obtained. Those skilled in the art will appreciate that the fluid line 24 alternatively may be provided below the test tool, in which case the piston 20 may be initially positioned adjacent the lower end cap 16 and thus move upward toward the upper end cap as the sample is taken.

Figure 6:
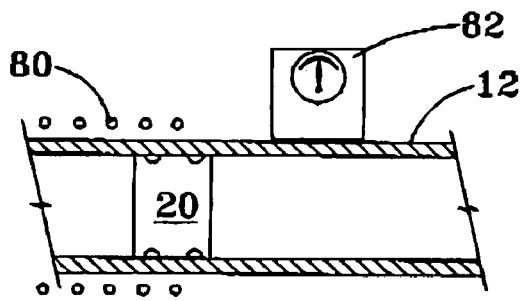
FIG. 6 illustrates a portion of a sample cylinder with a ferrous material piston and a magnetic test tool external of the cylinder.

In the FIG. 6 embodiment, a non-ferrous material cylinder 12 may be used in conjunction with a ferrous material piston 20. Once the sampling system or test tool 10 is returned to the surface, a transformer coil 80 or other magnetic test tool 82 may be axially moved external of the cylinder 12 to determine the position of the ferrous piston 20 within the non-ferrous cylinder. In the FIG. 2 embodiment, the central member 15 may be fabricated from a non-ferrous material to reduce interference if used with the FIG. 6 piston measurement technique.

Figure 7:
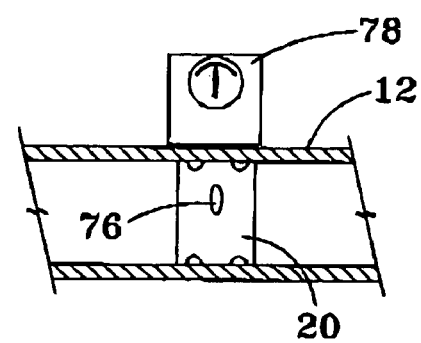
FIG. 7 illustrates a portion of the sample cylinder and a radioactive pellet on the piston with a sensor external of the cylinder responsive to the position of the pellet.

In the FIG. 7 embodiment, a radioactive pellet 76 is provided on the piston 20, and a radioactive sensor 78 external of the cylinder may be used to determine the position of the pellet and thus the position of the piston 20 within the cylinder. This embodiment is thus similar to the FIG. 5 embodiment.

Figure 8:
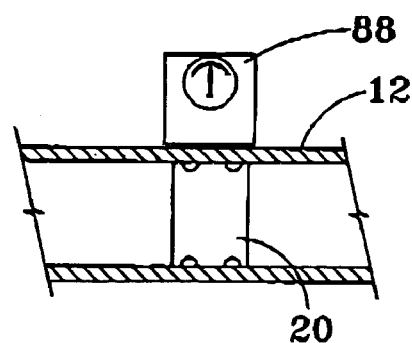
FIG. 8 illustrates an acoustic sensor for detecting an interface between fluid in the cylinder and the solid material of the piston.

In the FIG. 8 embodiment, an acoustic sensor 88 external of the cylinder may be responsive to the difference between fluid within the cylinder 12 and the solid material of the piston 20 to determine the fluid/piston interface and thereby determine the position of the piston within the cylinder.

Different embodiments for determining the position of the piston 20 within the cylinder 12 as shown in FIGS. 5–8 may thus be used with the various sampling systems shown in FIGS. 1–4.

A fluid separation device other than a piston may be used within the cylinder to separate the sampled fluid from the buffering fluid. As a practical matter, however, the desired relatively small diameter of the cylinder 12 as well as the length and thus the volume of fluid sampled would make it difficult for another type of displacement device, such as a bellows or diaphragm, to practically serve the function of the piston as disclosed herein.

Although specific embodiments of the invention have been described herein in some detail, this has been done solely for the purposes of explaining the various aspects of the invention, and is not intended to limit the scope of the invention as defined in the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

What is claimed is:

1. A formation test tool for positioning within a well to seal with a formation of interest and obtaining a downhole fluid sample from the formation of interest and returning the fluid sample to the surface of the well, comprising:
    a cylinder positionable within the well and forming a fluid sample chamber therein;
    a piston sealingly movable within the cylinder and separating the fluid sample from a cushioning fluid;
    a fluid line fluidly connecting the formation of interest to the fluid sample chamber when the tool is downhole;
    a packer element to seal with a sidewall of the formation while providing fluid communication between the formation and the flow line;
    a valve controlling fluid flow in the fluid line; and
    a magnet supported on the piston and outputting signals indicative of the magnet position within the fluid sample chamber and thus the volume of the fluid sample within the cylinder.

2. A formation test tool as defined in claim 1, further comprising:
    a meter movable exterior of the cylinder for determining the position of the magnet within the cylinder.

3. A formation test tool as defined in claim 1, wherein the magnet is a disk shaped magnet positioned within the separator piston.

4. A formation test tool as defined in claim 1, wherein the cylinder is fabricated from a nonmagnetic material.

5. A formation test tool as defined in claim 1, further comprising: a pump along the flow line for discharging fluid to the sample chamber.

6. A formation test tool as defined in claim 1, further comprising:
    a charging piston sealingly movable within the cylinder and separating a gas within the cylinder below the piston from wellbore fluid within the cylinder; and
    a port for fluid communication between the wellbore fluid within the cylinder from the wellbore fluid external of the cylinder.

7. A formation test tool for positioning within a well to seal with a formation of interest and obtaining a downhole fluid sample from the formation of interest and returning the fluid sample to the surface of the well, comprising:
    a cylinder positionable within the well and forming a fluid sample chamber therein;
    a piston sealingly movable within the cylinder and separating the fluid sample from a cushioning fluid;
    a fluid line fluidly connecting the formation of interest to the fluid sample chamber when the tool is downhole;
    one or more packer elements each to seal with a sidewall of the formation while providing fluid communication between the formation and the flow line;
    a valve controlling fluid flow in the fluid line; and
    a sensor for detecting a position of the piston within the cylinder while at the surface of the well.

8. A formation test tool as defined in claim 7, further comprising:
    a magnet supported within the piston; and
    the sensor is moveable exterior of the cylinder for determining the position of the magnet within the cylinder.

9. A formation test tool as defined in claim 7, further comprising:
    a pump along the flow line for discharging fluid to the sample chamber.

10. A method of positioning a tool within a well to seal with a formation of interest and obtaining the volume of the downhole fluid sample within a formation test tool at the surface, comprising:
    providing a cylinder positionable within the well and forming a fluid sample chamber therein;
    providing a piston sealingly movable within the cylinder and separating the fluid sample from a cushioning fluid;
    fluidly connecting the formation of interest to the fluid sample chamber while the tool is downhole;

sealing a sidewall of the formation while providing fluid communication between the formation and the flow line;
controlling fluid flow from the formation of interest to the cylinder; and
measuring a position of the piston within the cylinder at the surface to provide an indication of the volume of the fluid sample within the cylinder.

11. A method as defined in claim 10, further comprising:
supporting a magnet on the piston; and
moving a sensor exterior of the cylinder for determining a position of the magnet within the cylinder.

12. A method as defined in claim 10, further comprising:
forming the cylinder from a non-ferrous material;
forming the piston from the ferrous material; and
moving a magnetic tester exterior of the cylinder to determine a position of the piston within the cylinder.

* * * * *